United States Patent
Jomaa

(12) 
(10) Patent No.: US 6,696,427 B1
(45) Date of Patent: Feb. 24, 2004

(54) USE OF BISPHOSPHONATES FOR THE PREVENTION AND TREATMENT OF INFECTIOUS PROCESSES

(75) Inventor: Hassan Jomaa, Giessen (DE)

(73) Assignee: Jomaa Pharmaka GmbH, Giessen (DE)

( * ) Notice: Subject to any disclaimer, the term of this patent is extended or adjusted under 35 U.S.C. 154(b) by 0 days.

(21) Appl. No.: 09/868,961

(22) PCT Filed: Dec. 23, 1999

(86) PCT No.: PCT/EP99/10350
§ 371 (c)(1),
(2), (4) Date: Jun. 22, 2001

(87) PCT Pub. No.: WO00/38660
PCT Pub. Date: Jul. 6, 2000

(30) Foreign Application Priority Data

Dec. 23, 1998 (DE) .......................... 198 59 668

(51) Int. Cl.$^7$ ............................... A61K 31/66
(52) U.S. Cl. .......................................... 514/75
(58) Field of Search ............................ 514/75

(56) References Cited

U.S. PATENT DOCUMENTS

| 5,270,365 A | * | 12/1993 | Gertz et al. ............... 514/108 |
| 5,563,128 A | * | 10/1996 | Pauls et al. ................. 514/80 |
| 5,652,227 A | | 7/1997 | Pekka et al. |
| 6,114,316 A | * | 9/2000 | Ramamurthy et al. ...... 514/180 |

FOREIGN PATENT DOCUMENTS

| DE | 69218624 | 8/1997 |
| DE | 19738005 | 3/1999 |
| DE | 198 28 450 | 12/1999 |
| EP | 0221611 | 5/1987 |
| EP | 0 541 037 | 5/1993 |
| GB | 2 312 165 | 10/1997 |
| WO | WO97/43437 | 11/1997 |
| WO | 0001238 | 1/2000 |
| WO | WO00/01238 | 1/2000 |

OTHER PUBLICATIONS

Byington et al. (1997) "Entamoeba Histolytica: Computer–assisted Modeling of Phosphofructokinase for the Prediction of Broad–Spectrum Antiparasitic Agents" *Exp. Parasitol*, vol. 87(3) pp. 194–202.

Nicolai et al. (1995) "Also–Virus–Induced Paget's Disease can be Treated!" *Therapiewoche* vol. 31, pp. 1824–1827.

Fazio et al. (1988) "Antiviral Activity of 2 Inorganic Pyrophosphate Analogs Phosphonoacetic Acid PAA and Tetrasodium Carbonyl Biphosphonate TCB" *Fitopatologia Brasileira*, vol. 13, p. 114.

Sansoni et al. (1995) "Inhibition of Antigen–Presenting Cell Function by Alendronate in vitro" *Journal of Bone and Mineral Research*, vol. 10 (11), pp. 1719–1725.

Zojer et al. (1998) "Effects of Bisphosphonate Treatment on Lymphocyte Subsets", *Annals of Hematology*, vol. 77, pp. 572.

Kunzmann et al. (1997) "Stimulation of Human Gammadelta T Cells by Aminobisphosphonates used in Treatment of Bone Disorders", vol. 90 (10), pp. 575A.

Kunzmann et al. (1997) "Bisphosphonates used in Treatment of Bone Disorders Stimulate Human, Gamma..Delta. T cells" *Immunobiology*, vol. 197 p. 221.

Kunzmann et al. (1998) "Pamidronate Induces Gamamdelta T cell Expansion in vivo and Mediates Anti–Plasma Cell Activity in Multiple Myeloma" *Blood*, vol. 92 (10), p. 279B.

* cited by examiner

*Primary Examiner*—Deborah Lambkin
(74) *Attorney, Agent, or Firm*—Harness, Dickey & Pierce, P.L.C.

(57) ABSTRACT

The invention relates to the use of bisphosphonic acids of general formula (I) and derivatives thereof for the therapeutic and prophylactic treatment of infectious processes caused by viruses, bacteria, fungi or parasites in humans and animals, by deactivating the γδT cells.

14 Claims, No Drawings

USE OF BISPHOSPHONATES FOR THE PREVENTION AND TREATMENT OF INFECTIOUS PROCESSES

CROSS REFERENCE TO RELATED APPLICATIONS

Applicant claims priority under 35 U.S.C. §119 of German Application No. 198 59 668.5 filed Dec. 23, 1998. Applicant also claims priority under 35 U.S.C. §120 of PCT/EP99/10350 filed Dec. 23, 1999. The international application under PCT article 21(2) was not published in English.

This invention relates to the inactivation of γδ-T cells, inter alia by the use of bisphosphonates for the therapeutic and prophylactic treatment of infections in humans and animals which are caused by viruses, bacteria, fungi and parasites.

The use of bisphosphonic acids and some of the derivatives thereof in pharmaceutical preparations is already known. The microbiostatic activity of bisphosphonic acids (DE 3 611 522), their activity in the treatment of disorders of calcium and phosphate metabolism (DE 2 534 390, DE 2 534 391, DE 3 334 211, DE 3 434 667, DE 2 745 083), their cytostatic activity (DE 3 425 812), their lipid-reducing activity (Arzneimittelforschung 46, 759–62) and their ability to stimulate immune cells WO 97/38 696) are already known.

In order to widen the range of options for treating humans and animals, there is an urgent requirement to provide agents which are highly active.

The object of the present invention is accordingly to provide a substance which is universally usable in infections by viruses, bacteria, fungi and parasites in humans and animals and which meets the above-stated requirements.

This object is utterly surprisingly achieved by the group of substances defined in claim 2. This group of substances exhibits antiinfective action against viruses, bacteria, fungi, uni- and multicellular parasites.

The immune system protects humans and animals from tumours, infections etc. When the body is confronted with an immunogen (for example constituents of a microorganism), this brings about the multiplication and maturation of cells which are capable of combating this immunogen. Only one part of the immune system effects the actual specific immune response, with a second regulatory part providing assistance. Immunosuppression is a function of the regulatory components. These cells prevent the immune reaction from exceeding certain limits. Certain T cell populations, such as the γδ-T cells, are able to effect this immunosuppression (McMenamin et al., Science Sep. 23, 1994; 265(5180): 1869–71). These cells are stimulated by various microorganisms (Jomaa et al. FEMS Immunol. Med. Microbiol. September 1999; 25(4); 371–8). This group of pathogens includes *Plasmodium falciparum*, the causative organism of malaria, *Mycobacterium tuberculosis*, the causative organism of *tuberculosis*, and the Epstein-Barr virus, the causative organism of mononucleosis. These pathogens hold the immune system in check by simulating immunosuppressive γδ-T cells, which means that no proper immune defence comes into effect. As a result, the microorganisms are able to exist in the host and persist for a very long time.

It has now been found that substances of the general formula (I)

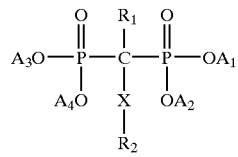

in which

A$_1$, A$_2$, A$_3$, A$_4$, which may be identical or different, are selected from the group which consists of hydrogen, metals of main groups I, II and III of the periodic system, such as Na, K, Ca, Mg, Al as well as substituted and unsubstituted ammonium and ammonium compounds derived from ethylenediamine or amino acids, X is absent or is selected from the group which consists of alkylene with up to 9 carbon atoms, alkenylene with up to 9 carbon atoms, hydroxyalkylene with up to 9 carbon atoms and amidino, R$_1$ is selected from the group which consists of H, OH, NH$_2$, —CH$_3$, R$_2$ is selected from the group which consists of H, OH, —NH$_2$, substituted and unsubstituted acyl, substituted and unsubstituted alkyl, substituted and unsubstituted aryl, substituted and unsubstituted cycloalkyl, substituted and unsubstituted aralkyl, substituted and unsubstituted heterocyclic residue and the pharmaceutically compatible salts, amides, esters and salts of the esters or compounds which, on administration, form the compounds to be administered as metabolites or breakdown products, result in inactivation of the γδ-T cells in humans and animals. These substances are accordingly suitable for the treatment and prophylaxis of infectious diseases caused by parasites, bacteria and viruses. In particular, these substances are suitable for the eradication of persistent infectious organisms including *Helicobacter pylori*, Chlamydia and hepatitis C virus.

These substances are furthermore suitable as an adjuvant to vaccines to strengthen the immune response to vaccinations.

Preferably suitable substances of the formula (I) are those in which

A$_1$, A$_2$, A$_3$, A$_4$, which may be identical or different, are selected from the group which consists of hydrogen, metals of main groups I, II and III of the periodic system, such as Na, K, Ca, Mg, Al, substituted and unsubstituted ammonium and ammonium compounds derived from ethylenediamine or amino acids, X is absent or is selected from the group which consists of alkyl, (CH$_2$)$_{1-6}$, in particular (CH$_2$)$_{1-5}$, and amidino, R$_1$ is selected from the group which consists of H, OH, NH$_2$, —CH$_3$, and R$_2$ is selected from the group which consists of

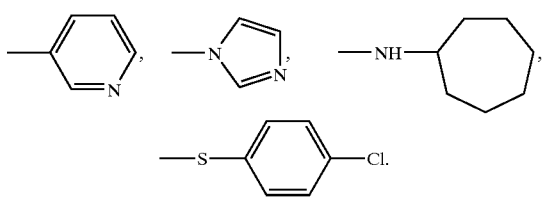

Special features of the above definitions and suitable examples thereof are given below:

"Acyl" is a substituent which originates from an acid, such as from an organic carboxylic acid, carbonic acid, carbamic acid or the thio acid or imidic acid corresponding to the above individual acids, or from an organic sulfonic acid, wherein these acids in each case comprise aliphatic, aromatic and/or heterocyclic groups in the molecule together with carbamoyl or carbarmimidoyl.

Suitable examples of these acyl groups are given below.

Aliphatic acyl groups are defined as acyl residues originating from an aliphatic acid and include the following:
 alkanoyl (for example formyl, acetyl, propionyl, butyryl, isobutyryl, valeryl, isovaleryl, pivaloyl etc.); alkenoyl (for example acryloyl, methacryloyl, crotonoyl etc.); alkylthioalkanoyl (for example methylthioacetyl, ethylthioacetyl etc.); alkanesulfonyl (for example mesyl, ethanesulfonyl, propanesulfonyl etc.); alkoxycarbonyl (for example methoxycarbonyl, ethoxycarbonyl, propoxycarbonyl, isopropoxycarbonyl, butoxycarbonyl, isobutoxycarbonyl etc.); alkylcarbamoyl (for example methylcarbamoyl etc.); (N-alkyl)thiocarbamoyl (for example (N-methyl)thiocarbamoyl etc.); alkylcarbamimidoyl (for example methylcarbamimidoyl etc.); oxalo; alkoxalyl (for example methoxalyl, ethoxalyl, propoxalyl etc.).

In the above examples of aliphatic acyl groups, the aliphatic hydrocarbon moiety, in particular the alkyl group or alkane residue, may optionally have one or more suitable substituents, such as amino, halogen (for example fluorine, chlorine, bromine etc.), hydroxy, hydroxyimino, carboxy, alkoxy (for example methoxy, ethoxy, propoxy etc.), alkoxycarbonyl, acylamino (for example benzyloxycarbonylamino etc.), acyloxy (for example acetoxy, benzoyloxy etc.) and the like; preferred aliphatic acyl residues with such substituents which may be mentioned are, for example, alkanoyls substituted with amino, carboxy, amino and carboxy, halogen, acylamino or the like.

Aromatic acyl residues are defined as those acyl residues which originate from an acid with a substituted or unsubstituted aryl group, wherein the aryl group may comprise phenyl, tolyl, xylyl, naphthyl and the like; suitable examples are stated below:
 aroyl (for example benzoyl, toluoyl, xyloyl, naphthoyl, phthaloyl etc.); aralkanoyl (for example phenylacetyl etc.); aralkenoyl (for example cinnamoyl etc.); aryloxyalkanoyl (for example phenoxyacetyl etc.); arylthioaikanoyl (for example phenylthioacetyl etc.); arylaminoalkanoyl (for example N-phenylglycyl, etc.); arenesulfonyl (for example benzenesulfonyl, tosyl or toluenesulfonyl, naphthalenesulfonyl etc.); aryloxycarbonyl (for example phenoxycarbonyl, naphthyloxycarbonyl etc.); aralkoxycarbonyl (for example benzyloxycarbonyl etc.); arylcarbamoyl (for example phenylcarbamoyl, naphthylcarbamoyl etc.); arylglyoxyloyl (for example phenylglyoxyloyl etc.).

In the above-stated Examples of aromatic acyl residues, the aromatic hydrocarbon moiety (in particular the aryl residue) and/or the aliphatic hydrocarbon moiety (in particular the alkane residue) may optionally have one or more suitable substituents, such as those which have already been stated as suitable substituents for the alkyl group or the alkane residue. Examples of preferred aromatic acyl residues with specific substituents which may in particular be mentioned are aroyl substituted with halogen and hydroxy or with halogen and acyloxy, and aralkanoyl substituted with hydroxy, hydroxyimino, dihaloalkanoyloxyimino, together with arylthiocarbamoyl (for example phenylthiocarbamoyl etc.); arylcarbamimidoyl (for example phenylcarbarmimidoyl etc.).

A heterocyclic acyl residue is taken to mean an acyl residue which originates from an acid with a heterocyclic group; such residues include:
 heterocyclic carbonyl, in which the heterocyclic residue is an aromatic or aliphatic 5- to 6-membered heterocycle with at least one heteroatom from the group nitrogen, oxygen and sulfur (for example thiophenyl, furoyl, pyrrolecarbonyl, nicotinyl etc.);
 heterocycle-alkanoyl, in which the heterocyclic residue is 5- to 6-membered and comprises at least one heteroatom from the group nitrogen, oxygen and sulfur (for example thiophenylacetyl, furylacetyl, imidazolylpropionyl, tetrazolylacetyl, 2-(2-amino-4-thiazolyl)-2-methoxyiminoacetyl etc.) and the like.

In the above Examples of heterocyclic acyl residues, the heterocycle and/or the aliphatic hydrocarbon moiety may optionally comprise one or more suitable substituents, such as the same as were stated to be suitable for alkyl and alkane groups.

"Alkyl" is a linear or branched alkyl residue with up to 9 carbon atoms, such as methyl, ethyl, propyl, isopropyl, butyl, isobutyl, tert.-butyl, pentyl, hexyl and the like.

Cycloalkyl preferably denotes an optionally substituted $C_3$-$C_7$ cycloalkyl; possible substituents are inter alia alkyl, alkenyl, alkynyl, alkoxy (for example methoxy, ethoxy etc.), halogen (for example fluorine, chlorine, bromine etc.), nitro and the like.

Aryl is an aromatic hydrocarbon residue, such as phenyl, naphthyl etc., which may optionally comprise one or more suitable substituents, such as alkyl, alkenyl, alkynyl, alkoxy (for example methoxy, ethoxy etc.), halogen (for example fluorine, chlorine, bromine etc.), nitro and the like.

"Aralkyl" includes mono-, di-, triphenylalkyls such as benzoyl, phenethyl, benzhydryl, trityl and the like, wherein the aromatic moiety may optionally comprise one or more suitable substituents, such as alkoxy (for example methoxy, ethoxy etc.), halogen (for example fluorine, chlorine, bromine etc.), nitro and the like.

"Alkylene" includes linear or branched alkylene groups, which comprise up to 9 carbon atoms and may be represented by the formula

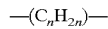
—($C_nH_{2n}$)— in which n is an integer from 1 to 9, such as methylene, ethylene, trimethylene, methylethylene, tetramethylene, 1-methyltrimethylene, 2-ethylethylene, pentamethylene, 2-methyltetramethylene, isopropylethylene, hexamethylene and the like; preferred alkylene residues have up to 4 carbon atoms and particularly preferred residues are those with 3 carbon atoms, such as for example trimethylene.

"Alkenylene" includes linear or branched alkenylene groups having up to 9 carbon groups which may be represented by the formula $$-(C_nH_{2n-2})-$$

in which n is an integer from 2 to 9, such as for example vinylene, propenylene (for example 1-propenylene, 2-propenylene), 1-methylpropenylene, 2-methylpropenylene, butenylene, 2-ethylpropenylene, pentenylene, hexenylene and the like; the alkenylene residue may particularly preferably have up to 5 carbon atoms and in particular 3 carbon atoms, such as for in example 1-propenylene.

"Hydroxyalkylene" includes linear or branched alkylene residues, which have up to 9 carbon atoms, wherein one or more selected carbon atoms is/are substituted with a hydroxy group; these residues may be reproduced by the formula $$-(C_nH_{2n-z})(OH)_z-$$

in which n is an integer from 1 to 9 and z is an integer from 1 to 9, where $z \leq n$ applies. Suitable examples of hydroxyalkylene groups are hydroxymethylene, hydroxyethylene (for example 1-hydroxyethylene and 2-hydroxyethylene), hydroxytrimethylene (for example 1-hydroxytrimethylene, 2-hydroxytrimethylene and 3-hydroxytrimethylene), hydroxytetramethylene (for example 2-hydroxytetramethylene), 2-hydroxy-2-methyltrimethylene, hydroxypentamethylene (for example 2-hydroxypentamethylene), hydroxyhexamethylene (for example 2-hydroxyhexamethylene) and the like. A particularly preferred hydroxyalkylene is one comprising up to 4 carbon atoms and in particular such a compound comprising 3 carbon atoms, such as for example hydroxytrinethylene.

"Heterocyclic residue" is preferably an aromatic or aliphatic 5- to 6-membered heterocycle with at least one heteroatom from the group nitrogen, oxygen and sulfur (for example thiophenyl, furoyl, pyrrolecarbonyl, nicotinoyl etc.).

The following have proved to be particularly active bisphosphonic acids amino-hydroxy-methylidene-bisphosphonic acid (AMP),
2-amino-1-hydroxyethylidene-1,1-bisphosphonic acid (AEP),
3-amino-1-hydroxypropylidene-1,1-bisphosphonic acid (pamidronic acid),
4-amino-1-hydroxybutylidene-1,1-bisphosphonic acid (alendronic acid),
6-amino-1-hydroxyhexylidene-1,1-bisphosphonic acid (AHP),
amidinomethylene-bisphosphonic acid (AIMP),
3-methylpentylamino-1-hydroxypropylidene-1,1-bisphosphonic acid (ibandronic acid),
2-(3-pyridinyl)-1-hydroxyethylidene-bisphosphonic acid (risedronic acid),
1-hydroxy-2-(imidazol-1-yl)-ethylidene-1,1-bisphosphonic acid (zoledronic acid), cycloheptylaminomethylenediphosphonic acid (cimadronic acid),
4-chlorophenyl-thiomethylene-1,1-bisphosphonic acid (tiludronic acid) and the derivatives thereof.

The compounds are in particular suitable for the therapeutic and prophylactic treatment of infections in humans and animals caused by viruses, bacteria, uni- and multicellular parasites and fungi.

The bisphosphonic acids and the derivatives thereof are suitable for the treatment of acne vulgaris, *tuberculosis* in humans and animals, leprosy and further mycobacterioses in humans and animals, paratuberculosis in animals, Campylobacter enteritis infections in humans and animals.

Use is furthermore in particular preferred in the eradication of Helicobacter in ulcers of the gastrointestinal tract.

The substances are furthermore in particular suitable for the eradication of Chlamydia for the prevention or treatment of cardiac and vascular diseases, in particular coronary cardiac disease.

Combination treatment with another antibiotic may also be used to treat the above-stated diseases. Isoniazid, rifampicin, ethambutol, pyrazinamide, streptomycin, protionamide and dapsone are in particular suitable for combination preparations with other antiinfective agents for the treatment of *tuberculosis*.

The bisphosphonates according to the invention are suitable for combating the following viral infections:

eradication of papillomaviruses to prevent tumours, in particular tumours of the reproductive organs caused by papillomaviruses in humans, eradication of herpesviruses, eradication of human herpesvirus 8 to treat Kaposi's sarcoma, eradication of cytomegaloviruses before transplantations, eradication of Epstein-Barr viruses before transplantation and to prevent tumours associated with Epstein-Barr viruses, eradication of hepatitis viruses to treat chronic liver disease and to prevent liver tumours and cirrhosis of the liver, eradication of coxsackie-viruses in cardiomyopathy, eradication of coxsackie-viruses in diabetes mellitus patients, eradication of immunodeficiency viruses in humans and animals, treatment of accompanying infections in AIDS patients, treatment of respiratory tract inflammation of viral causation (laryngeal papilloma, hyperplasia, rhinitis, pharyngitis, bronchitis, pneumonia), of the liver and gall system (hepatitis, cholangitis, hepatocellular carcinoma), of the lymphatic tissue (mononucleosis, lymphadenitis), of the haemopoietic system, of the skin (warts, dermatitis, herpes labialis, herpes febrilis, herpes zoster, shingles), of the mucous membranes (papillomas, conjunctival papillomas, hyperplasia, dysplasia), of the cardiovascular system (arteriitis, myocarditis, endocarditis, pericarditis), of the kidney/urinary system, of the reproductive organs (anogenital lesions, warts, genital warts, sharp condylomas, dysplasia, papillomas, cervical dysplasia, condyloma acuminatum, epidermodysplasia verruciformis), of the locomotory organs (myositis, myalgia).

The agents may be used in combination with other agents having antiviral properties.

Preferred pharmaceutical preparations which may be mentioned are tablets, coated tablets, capsules, pills, granules, suppositories, solutions, suspensions and emulsions, pastes, ointments, gels, creams, lotions, powders and sprays. Tablets, coated tablets, capsules, pills and granules may contain the active substances together with conventional excipients, such as (a) fillers and extenders, for example starches, lactose, cane sugar, glucose, mannitol and silica, (b) binders, for example carboxymethylcellulose, alginates, gelatine, polyvinylpyrrolidone, (c) humectants, for example glycerol, (d) suspending agents, for example agar-agar, calcium carbonate and sodium carbonate, (e) dissolution retardants, for example paraffin and (f) resorption accelerators, for example quaternary ammonium compounds, (g) wetting agents, for example cetyl alcohol, glycerol monostearate, (h) adsorbents, for example kaolin and bentonite and (i) lubricants, for example talcum, calcium and magnesium stearate and solid polyethylene glycols or mixtures of the substances stated in (a) to (i).

The tablets, coated tablets, capsules, pills and granules may be provided with conventional coatings and shells optionally containing opacifying agents and may also be composed such that they release the active substances only with a delay or preferably in a particular part of the intestinal tract, wherein polymeric substances and waxes may, for example, be used as the matrices.

The active substance or substances, optionally together with one or more of the above-stated excipients, may also be present in microencapsulated form.

In addition to the active substance or substances, suppositories may contain conventional water-soluble or water-insoluble excipients, for example polyethylene glycols, fats, for example cocoa butter and higher esters (for example $C_{14}$ alcohol with $C_{16}$ fatty acid) or mixtures of these substances.

In addition to the active substance or substances, ointments, pastes, creams and gels may contain conventional excipients, for example animal and vegetable fats, waxes, paraffins, starch, gum tragacanth, cellulose derivatives, polyethylene glycols, silicones, bentonites, silica, talcum and zinc oxide or mixtures of these substances.

In addition to the active substance or substances, powders and sprays may contain conventional excipients, for example lactose, talcum, silica, aluminium hydroxide, calcium silicate and polyamide powder or mixtures of these substances. Sprays may additionally contain conventional propellants, for example chlorofluorocarbons.

In addition to the active substance or substances, solutions and emulsions may contain conventional excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, peanut oil, corn oil, olive oil, castor oil and sesame oil, glycerol, glycerol formal, tetrahydrofurfuryl alcohol, polyethylene glycols and sorbitan fatty acid esters or mixtures of these substances.

For parenteral administration, the solutions and emulsions may also be present in sterile, isotonic form.

In addition to the active substance or substances, suspensions may contain conventional excipients, such as liquid diluents, for example water, ethyl alcohol, propylene glycol, suspending agents, for example ethoxylated isostearyl alcohols, polyoxyethylene sorbitol and sorbitan esters, microcrystalline cellulose, aluminium metahydroxide, bentonite, agar-agar and gum tragacanth or mixtures of these substances.

The stated formulations may also contain colorants, preservatives and odour- or flavour-enhanced additives, for example peppermint oil and eucalyptus oil, and sweeteners, for example saccharin.

Bisphosphonic acids and the derivatives thereof of the formula (I) should preferably be present in the pharmaceutical preparations listed above in a concentration of approx. 0.1 to 99.5 wt. %, preferably from approx. 0.5 to 95 wt. %, of the complete mixture.

Apart from the compounds of the formula (I), the pharmaceutical preparations listed above may also contain further pharmaceutical active substances.

The above-stated pharmaceutical preparations are produced in the conventional manner using known methods, for example by mixing the active substance or substances with the excipient or excipients.

The stated preparations may be administered to humans and animals orally, rectally, parenterally (intravenously, intramuscularly, subcutaneously), intracisternally, intravaginally, intraperitoneally, topically (powders, ointments, drops) and for the treatment of infections in cavities, body cavities. Suitable preparations which may be considered are solutions for injections, solutions and suspensions for oral therapy, gels, infusion formulations, emulsions, ointments or drops. Topical treatment may be performed using ophthalmological and dermatological formulations, silver and other salts, ear drops, eye ointments, powders or solutions. Administration to animals may also be achieved via the feed or drinking water in suitable formulations. Gels, pulverulent formulations, powders, tablets, controlled-release tablets, premixes, concentrates, granules, pellets, tablets, boli, capsules, aerosols, sprays, inhalation formulations may also be used in humans and animals. The compounds according to the invention may also be incorporated into other supports, such as for example plastics (plastic chains for topical treatment), collagen or bone cement.

There is a very wide range of variation in the quantity of the individual derivatives necessary to achieve the desired effect. It has in general proved advantageous in both human and veterinary medicine to administer the bisphosphonates of the formula (I) in total quantities of approx. 0.005 to approx. 200 mg/kg body weight per 24 hours, optionally in the form of two or more individual doses in order to achieve the desired results. An individual dose preferably contains the active substance or substances in quantities of approx. 0.002 to approx. 50 mg/kg body weight. It may, however, be necessary to deviate from the stated dosages, in particular as a function of the nature and body weight of the patient to be treated, the nature and severity of the disease, the nature of the preparations and the route of administration of the pharmaceutical preparation and the period of time over which administration is performed.

In some cases, it may accordingly be sufficient to use less than the above-stated quantity of active substance, while in other cases more than the above-stated quantity of active substance must be used. The person skilled in the art will use his/her skill to determine the optimum dosage and route of administration required in each particular case.

Animals may be treated with the compounds used according to the invention by administration in conventional concentrations and preparations together with feed or feed preparations or with drinking water.

Some examples of activity are listed below:

EXAMPLE 1

Healthy test subjects received an infusion of 90 mg of pamidronic acid at fortnightly intervals. After the third infusion, a blood sample was taken from the subjects. The mononuclear cells were isolated from the blood. The activatability of the $\gamma\delta$-T cells was then tested. A full description is published in Jomaa et al. FEMS Immunol. Med. Microbiol. September 1999; 25(4); 371–8.

The cells from the treated subjects exhibit no $\gamma\delta$-T cell activation by antigens obtained from microorganisms. In contrast, cells from control subjects could be activated.

EXAMPLE 2

The cells of test subjects who had been treated with ibandronic acid (1 mg per treatment) in accordance with the protocol from Example 1 exhibited no $\gamma\delta$-T cell activation by antigens which had been obtained from microorganisms.

EXAMPLE 3

The cells of test subjects who had been treated with zoledronic acid in accordance with the protocol from Examples 1 and 2 exhibited no $\gamma\delta$-T cell activation by antigens which had been obtained from microorganisms.

I claim:

1. A method for treating diseases caused by infectious agents comprising:
   administering to a patient in need of treatment an effective amount of at least one bisphosphonic acid having the general formula $$A_3O-\underset{\underset{OA_4}{|}}{\overset{\overset{O}{\|}}{P}}-\underset{\underset{\underset{R_2}{|}}{X}}{\overset{\overset{R_1}{|}}{C}}-\underset{\underset{OA_2}{|}}{\overset{\overset{O}{\|}}{P}}-OA_1 \qquad (I)$$

wherein
$A_1, A_2, A_3, A_4$, which may be identical or different, are selected from the group consisting of hydrogen, metals of main groups I, II and III of the periodic table substituted ammonium compounds, unsubstituted ammonium compounds and ammonium compounds derived from ethylenediamine or amino acids,
X is absent or is selected from the group consisting of alkylene with up to 9 carbon atoms, alkenylene with up to 9 carbon atoms, hydroxyalkylene with up to 9 carbon atoms and amidino,
$R_1$ is selected from the group consisting of H, OH, $NH_2$ and $-CH_3$,
$R_2$ is selected from the group consisting of H, OH, $-NH_2$, substituted and unsubstituted acyl, substituted and unsubstituted alkyl, substituted and unsubstituted aryl, substituted and unsubstituted cycloalkyl, substituted and unsubstituted aralkyl, substituted and unsubstituted heterocyclic residue and pharmaceutically compatible salts, amides, esters and salts of the esters, wherein when $R_2$ is a substituted or unsubstituted aryl or a substituted or unsubstituted aralkyl, $R_2$ contains a single substituted or unsubstituted aryl or aralkyl,
   wherein the at least one bisphosphonic acid inactivates γδ-T cells.

2. The method according to claim 1, wherein $A_1, A_2, A_3, A_4$, which may be identical or different, are selected from the group consisting of hydrogen, metals of main groups I, II and III of the periodic system, substituted and unsubstituted ammonium compounds and ammonium compounds derived from ethylenediamine or amino acids,
   X is absent or is selected from the group consisting of alkyl, $(CH_2)_{1-6}$ and amidino,
   $R_1$ is selected from the group consisting of H, OH, $NH_2$ and $-CH_3$, and
   $R_2$ is selected from the group consisting of $-NH_2$.

$$-N\underset{(CH_2)_4CH_3}{\overset{CH_3}{\diagup}}, \quad \text{3-pyridinyl}, \quad \text{imidazolyl},$$

$$-HN-\text{cycloheptyl} \quad \text{and} \quad -S-\text{C}_6\text{H}_4-Cl.$$

3. The method according to claim 2, wherein the at least one bishosphonic acid is selected from the group consisting of amino-hydroxymethylidene-bisphosphonic acid, 2-amino-1-hydroxyethylidene-1,1-bisphosphonic acid, 3-amino-1-hydroxypropylidene-1,1-bisphosphonic acid, 4-amino-1-hydroxybutylidene-1,1-bisphosphonic acid, 6-amino-1-hydroxyhexylidene-1,1-bisphosphonic acid, amidinomethylene-bisphosphonic acid, 3-methylpentylamino-1-hydroxypropylidene-1,1-bisphosphonic acid, 2-(3-pyridinyl)-1-hydroxyethylidene-bisphosphonic acid, 1-hydroxy-2-(imidazol-1-yl)-ethylidene-1,1-bisphosphonic acid, cycloheptylaminomethylenediphosphonic acid, 4-chlorophenylthiomethylene-1,1-bisphosphonic acid and derivatives thereof.

4. The method according to claim 1, wherein the disease is selected from the group consisting of acne vulgaris, *tuberculosis* in humans and animals, leprosy, mycobacterioses in humans and animals, paratuberculosis in animals, Campylobacter enteritis infections in humans and animals, Helicobacter pylori infections, Chlamydia, cardiac diseases and vascular diseases.

5. The method according to claim 1, wherein the at least one bisphosphonic acid eradicates bacteria and viruses.

6. The method according to claim 5, wherein the at least one bisphosphonic acid eradicates Helicobacter pylori and Chlamydia.

7. The method according to claim 5, wherein the at least one bisphosphonic acid eradicates papillomaviruses to prevent tumors, eradicates herpesviruses, eradicates cytomegaloviruses before transplantations, eradicates Epstein-Barr viruses before transplantation and to prevent tumors associated with Epstein-Barr viruses, eradicates hepatitis viruses to treat chronic liver disease and to prevent liver tumors and cirrhosis of the liver, eradicates coxsackie-viruses in cardiomyopathy, eradicates coxsackie-viruses in diabetes mellitus patients, eradicates immunodeficiency viruses in humans and animals, treats accompanying infections in AIDS patients, treats viral respiratory tract inflammation, treats viral infections of the liver and gall system, treats viral infections of lymphatic tissue, treats viral infections of the haemopoietic system, treats viral infections of skin, treats viral infections of mucous membranes, treats viral infections of the cardiovascular system, treats viral infections of the kidney and urinary system, and treats viral infections of reproductive organs.

8. The method according to claim 7, wherein the at least one bisphosphonic acid eradicates hepatitis C virus.

9. A composition for the treatment of diseases caused by infectious agents comprising:
   at least one bisphosphonic acid having the general formula $$A_3O-\underset{\underset{OA_4}{|}}{\overset{\overset{O}{\|}}{P}}-\underset{\underset{\underset{R_2}{|}}{X}}{\overset{\overset{R_1}{|}}{C}}-\underset{\underset{OA_2}{|}}{\overset{\overset{O}{\|}}{P}}-OA_1 \qquad (I)$$

wherein
$A_1, A_2, A_3, A_4$, which may be identical or different, are selected from the group consisting of hydrogen, metals of main groups I, II and III of the periodic table, substituted ammonium compounds, unsubstituted ammonium compounds and ammonium compounds derived from ethylenediamine or amino acids,
X is absent or is selected from the group consisting of alkylene with up to 9 carbon atoms, alkenylene with up to 9 carbon atoms, hydroxyalkylene with up to 9 carbon atoms and amidino, $R_1$ is selected from the group consisting of H, OH, $NH_2$ and —$CH_3$, $R_2$ is selected from the group consisting of H, OH, —$NH_2$, substituted and unsubstituted acyl, substituted and unsubstituted alkyl, substituted and unsubstituted aryl, substituted and unsubstituted cycloalkyl, substituted and unsubstituted aralkyl, substituted and unsubstituted heterocyclic residue and pharmaceutically compatible salts, amides, esters and salts of the esters, wherein when $R_2$ is a substituted or unsubstituted aryl or a substituted or unsubstituted aralkyl, $R_2$ contains a single substituted or unsubstituted aryl or aralkyl, and a pharmaceutically acceptable excipient, wherein the at least one bisphosphonic acid inactivates γδ-T cells.

10. The composition according to claim 9, wherein the composition is an adjuvant to vaccines.

11. The method according to claim 1, wherein the metals of main groups I, II and III of the periodic table are selected from the group consisting of Na, K, Ca, Mg and Al.

12. The method according to claim 7, wherein the at least one bisphosphonic acid treats laryngeal papilloma, hyperplasia, rhinitis, pharyngitis, bronchitis, pneumoniahepatitis, cholangitis, hepatocellular carcinoma, mononucleosis, lymphadenitis, warts, dermatitis, herpes labialis, herpes febrilis, herpes zoster, shingles, conjunctival papillomas, hyperplasia, dysplasia, arteriitis, myocarditis, endocarditis, pericarditis, anogenital lesions, warts, genital warts, sharp condylomas, dysplasia, papillomas, cervical dysplasia, condyloma acuminatum, epidermodysplasia verruciformis, myositis and myalgia.

13. The method according to claim 1, wherein the infectious agents are selected from the group consisting of viruses, bacteria, parasites and fungi.

14. The composition according to claim 9, wherein the infectious agents are selected from the group consisting of viruses, bacteria, parasites and fungi.

* * * * *